US008816681B2

(12) United States Patent
Braun

(10) Patent No.: US 8,816,681 B2
(45) Date of Patent: Aug. 26, 2014

(54) METHOD AND DEVICE FOR DETECTING NEAR-SURFACE DEFECTS BY MEANS OF MAGNETIC LEAKAGE FLUX MEASUREMENT

(75) Inventor: Heinrich Braun, Reutlingen (DE)

(73) Assignee: Institut Dr. Foerster GmbH & Co. KG (DE)

( * ) Notice: Subject to any disclaimer, the term of this patent is extended or adjusted under 35 U.S.C. 154(b) by 810 days.

(21) Appl. No.: 12/988,167

(22) PCT Filed: Mar. 25, 2009

(86) PCT No.: PCT/EP2009/002153
§ 371 (c)(1),
(2), (4) Date: Oct. 15, 2010

(87) PCT Pub. No.: WO2009/127316
PCT Pub. Date: Oct. 22, 2009

(65) Prior Publication Data
US 2011/0037461 A1 Feb. 17, 2011

(30) Foreign Application Priority Data

Apr. 16, 2008 (DE) .......................... 10 2008 020 194

(51) Int. Cl.
*G01N 27/82* (2006.01)
*G01N 27/87* (2006.01)
(52) U.S. Cl.
CPC ...................................... *G01N 27/87* (2013.01)
USPC ............................ 324/240; 324/228; 324/238
(58) Field of Classification Search
USPC .................................................. 324/228, 240
See application file for complete search history.

(56) References Cited

U.S. PATENT DOCUMENTS

| 3,379,969 | A | 4/1968 | Zinke |
| 4,492,115 | A | 1/1985 | Kahil et al. |
| 4,602,212 | A | 7/1986 | Hiroshima et al. |
| 5,023,550 | A | 6/1991 | Yamazaki et al. |
| 5,257,158 | A * | 10/1993 | Smith ............................ 361/143 |
| 5,331,278 | A * | 7/1994 | Evanson et al. ............... 324/232 |
| 5,537,038 | A | 7/1996 | Ando |
| 2007/0247145 | A1 | 10/2007 | Zimmermann |
| 2008/0042645 | A1 | 2/2008 | Kaack et al. |

FOREIGN PATENT DOCUMENTS

| DE | 33 21 375 A1 | 12/1983 |
| DE | 10 2004 035 174 A1 | 2/2006 |
| DE | 10 2006 019 128 A1 | 10/2007 |
| GB | 2 157 439 A | 10/1985 |
| JP | 56-7054 | 1/1981 |
| JP | 63-45555 | 2/1988 |
| JP | 4-218764 | 8/1992 |
| JP | 8-278289 A | 10/1996 |
| JP | 2004-279248 | 10/2004 |
| JP | 2006-153856 | 6/2006 |
| WO | 02/06812 A1 | 1/2002 |

OTHER PUBLICATIONS

A.I. Pashagin et al., "Magnetic Fields of Surface Flaws With Combined Magnetization of Products," Soviet Journal of Nondestructuve Testing USA, vol. 19, No. 2, Feb. 1983, pp. 144-150.
Hans Luz, "Inspection of Semi-finished Products Using the Magnetic High-frequency Stray-flux Method," Stahl u. Eisen 94 (Aug. 15, 1974) Nr. 17. pp. 814-818 (with translation).
Japanese Official Action dated Feb. 25, 2014 along with an English translation from corresponding Japanese Patent Application No. 2011-504340.
"Höchste Fehleranzeige—Empfindlichkeit an schwarzen Stahlstangen—mit dem Foerster-Circoflux®," Foerster, 7 pages including English Abstract.

* cited by examiner

*Primary Examiner* — Bot Ledynh
(74) *Attorney, Agent, or Firm* — DLA Piper LLP (US)

(57) ABSTRACT

In a method for detecting near-surface defects in a test sample consisting at least partly of a ferromagnetic material, a test volume of the test sample is magnetized and scanned for the detection of magnetic leakage fields caused by defects. The test volume is magnetized by means of a magnetic constant field and simultaneously by means of a magnetic alternating field superposed on the constant field. Leakage field test devices suitable for carrying out the method are described.

26 Claims, 5 Drawing Sheets

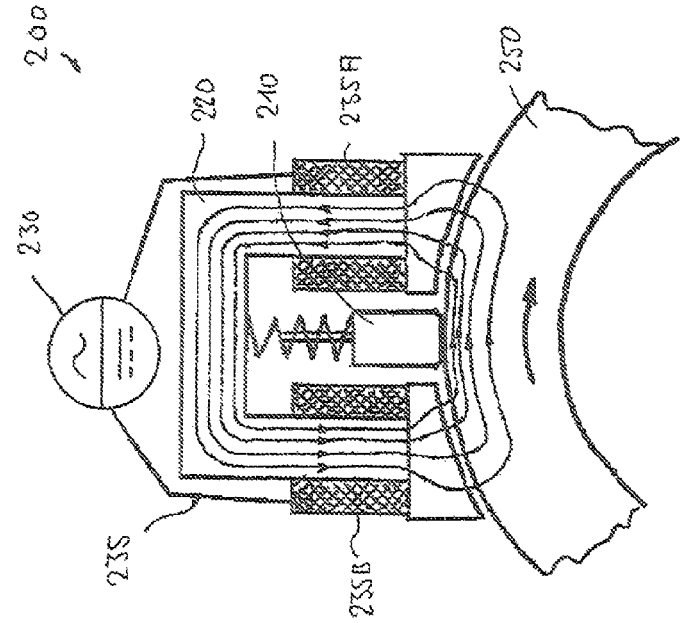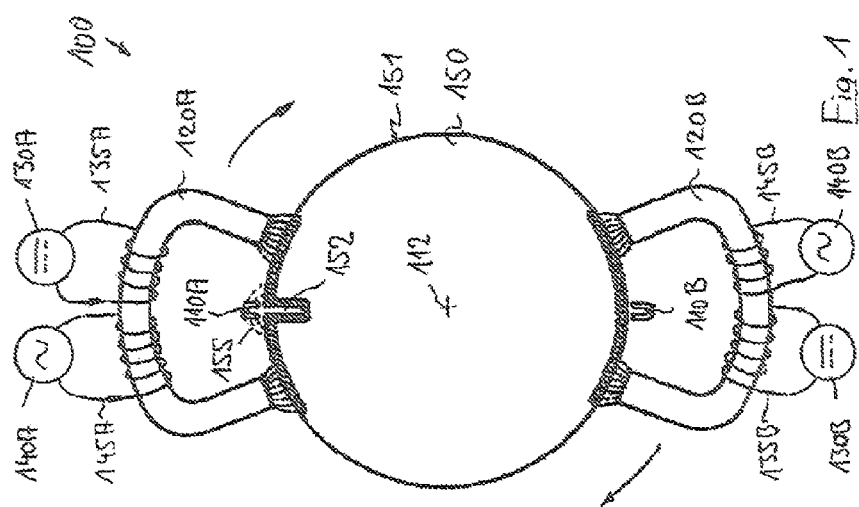
Fig. 1
Fig. 2

METHOD AND DEVICE FOR DETECTING NEAR-SURFACE DEFECTS BY MEANS OF MAGNETIC LEAKAGE FLUX MEASUREMENT

RELATED APPLICATIONS

This is a §371 of International Application No. PCT/EP2009/002153, with an international filing date of Mar. 25, 2009 (WO 2009/127316 A1, published Oct. 22, 2009), which is based on German Patent Application No. 10 2008 020 194.4, filed Apr. 16, 2008, the subject matter of which is incorporated by reference.

TECHNICAL FIELD

This disclosure relates to a method for detecting near-surface defects in a test sample consisting at least partly of a ferromagnetic material, and also to a device for detecting near-surface defects which is suitable for carrying out the method.

BACKGROUND

In the context of testing semifinished products for near-surface defects, magnetic leakage flux methods are an important component for monitoring quality in the process for producing the products. Magnetic leakage flux methods are less sensitive to some disturbing properties of semifinished products, such as, for example, roughness of the surface or scale coating, than the Eddy current method or ultrasonic testing, for example. This results in a better ratio between signal used and noise signal (S/N ratio), as a result of which more reliable fault identification is made possible.

In a device for detecting near-surface defects by leakage flux measurement, a test volume of the test sample is magnetized by a magnetization apparatus and scanned with the aid of at least one magnetic-field-sensitive test probe (leakage flux probe) for the detection of magnetic leakage fields caused by the defects.

The magnetic flux generated by a magnetization apparatus in the test sample is spatially distributed substantially homogeneously in the defect-free material. Cracks or other defects act as regions of increased magnetic resistance, and so field components in the vicinity of a defect are guided around the defect and also forced out from the metal in the region near the surface. The field components forced out are detected in the leakage flux methods for detecting the defects. In a leakage flux measurement, a near-surface defect (also called surface fault) is detectable when the field components displaced from the test sample reach as far as the region of the test probe and have a field strength sufficient for the detection.

The surface faults can be classified, e.g., according to their position in the material. There are near-surface defects, which reach as far as the surface of the test sample, that is to say, for example, cracks leading from the surface to within the material or cavities open to the surface, or the like. These can be referred to as "open faults" or "visible faults." However, there are also defects which lie concealed below a surface that appears more or less undisturbed, that is to say, for example, cracks in the depth of the material, such as stress cracks, or cracks which, although they reach as far as the surface in one production stage, have been closed again by near-surface deformation in a subsequent rolling process. These faults can be referred to as "concealed faults"; they are also referred to as "core faults" in the case of test samples composed of solid material and as "wall faults" in the case of tubular test samples.

The leakage flux test methods and test devices are subdivided, depending on how the material to be tested is magnetized, into methods and devices with constant field magnetization (DC leakage flux testing) and methods and devices with alternating field magnetization (AC leakage flux testing).

The methods with constant field magnetization are used in the testing of pipes, where both external faults, that is to say faults on the exterior side of the pipe, and internal faults, that is to say faults on the interior side of the pipe, are intended to be detected. A significant advantage of constant field magnetization is utilized here, namely the large penetration depth, such that internal faults can also be detected. In the case of very narrow and/or obliquely leading faults, by contrast, frequently only unsatisfactory test results are obtained.

A significant advantage of leakage flux methods with alternating field magnetization is the very high resolution for extremely small faults on the outer surface, that is to say for open faults. Therefore, the alternating field magnetization is generally employed when only exterior faults are intended to be detected, which is frequently the case for example with solid material such as round billets, square billets or bar steel. What is disadvantageous is that, as a result of the small penetration depth of the alternating field, deep faults which are not open to the surface (concealed faults) frequently can only be identified unsatisfactorily or cannot be identified at all.

DE 10 2004 035 174 B4 describes a method and a device for the nondestructive testing of pipes composed of ferromagnetic steel by leakage flux, wherein the pipe (test sample) is magnetized by a constant field. To enable better fault assignment between pipe outer surface and pipe inner surface, the amplitude of the horizontal field component of the magnetic leakage flux, the amplitude varying in the vertical direction, is detected firstly at a near-surface distance from the pipe outer surface and secondly at a distance further away from that and the detected signals are related to one another by means of difference formation, wherein the amplitude of the vertical field component of the magnetic leakage flux is also detected in addition and related to the amplitude of the horizontal field component measured at the near-surface distance and/or at the distance further away from that.

DE 10 2006 019 128 A1 describes a leakage flux measuring instrument for detecting near-surface and surface-distant defects on ferromagnetic test samples by leakage flux measurement, wherein the test sample is likewise magnetized by a magnetic constant field. To have the effect that the faults concealed below the material surface of the test sample can be detected better by means of leakage flux observation without reducing the sensitivity for near-surface faults, a combination of at least one flat coil or probe and at least one coil or probe oriented perpendicularly thereto is provided on the test probe side.

It could therefore be helpful to provide a method for detecting near-surface defects by leakage flux measurement and also a corresponding device which make it possible to detect both faults open to the surface and concealed faults with high sensitivity.

SUMMARY

I provide a method for detecting near-surface defects in a test sample consisting at lest partly of ferromagnetic material, wherein a test volume of the test sample is magnetized and scanned for the detection of magnetic leakage fields caused by defects, characterized in that the test volume is magnetized by a magnetic constant field and simultaneously by a magnetic alternating field superposed on the constant field.

I also provide a device for detecting near-surface defects in a test sample consisting at least partly of ferromagnetic material, including a magnetization apparatus for magnetizing a test volume of the test sample, and at least one magnetic-field-sensitive test probe, for the detection of magnetic leakage fields caused by defects, characterized in that the magnetization apparatus includes a constant field magnetization unit for generating a magnetic constant field and an alternating field magnetization unit for generating a magnetic alternating field superposed on the constant field in the test volume.

BRIEF DESCRIPTION OF THE DRAWINGS

FIG. 1 shows a schematic view of a rotary head system for the leakage flux testing of round material passing through.

FIG. 2 schematically shows a static leakage flux measuring system with combined AC/DC magnetization for testing rotating test samples.

DETAILED DESCRIPTION

Figure 3:
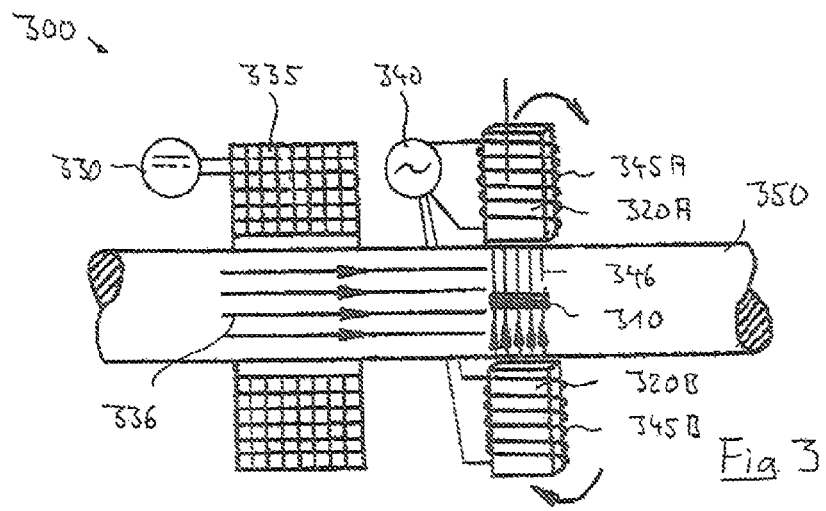
FIG. 3 schematically shows a side view of a rotating test system with alternating field magnetization rotating around the test sample and static constant field magnetization.

In a method for detecting near-surface defects in a test sample consisting at least partly of ferromagnetic material, a test volume of the test sample is magnetized by a magnetization apparatus and scanned by at least one magnetic-field-sensitive test probe for the detection of magnetic leakage fields caused by defects. In this case, the test volume is magnetized by a magnetic constant field and simultaneously by a magnetic alternating field superposed on the constant field.

In this case, the expression "test volume" denotes a volume region of the test sample which is magnetized with the aid of the superposed magnetic fields (alternating field and constant field) and which in this case simultaneously lies in the detection region of a (at least one) magnetic-field-sensitive test probe in such a way that magnetic leakage fields caused by defects situated within the test volume can be detected by the test probe.

A combined alternating field magnetization (AC magnetization) and constant field magnetization (DC magnetization) is thus used. It has been found that, by the combined AC/DC magnetization, the detection depth can be significantly increased in comparison with conventional alternating leakage flux methods without disadvantageously influencing the detection accuracy and high resolution for faults open to the surface. Given a suitable choice of the magnetization parameters, alternating leakage flux methods can thus yield significantly improved results if the test sample to be tested is additionally exposed to a magnetic constant field having a suitable magnitude. The improved detection sensitivity primarily for more deeply situated defects is attributed to the fact that, by virtue of the magnetic constant field acting in addition to the magnetic alternating field, the operating point of the magnetic testing on the material-specific hysteresis curve is shifted into a more favorable region. In this case, the strength of the magnetic constant field is advantageously apportioned such that the leakage flux mechanism for the alternating field, that is to say the mechanism of action of the alternating field testing, is substantially maintained in comparison with conventional alternating methods.

There have been attempts to improve the detection properties of the leakage flux method by complicated constructions of the leakage field probes. Limits are reached when the leakage field to be detected is too weak. In contrast thereto, I take a different path since origination of the measurement variable, that is to say of the leakage field to be detected, is influenced directly. Improved measurement results can therefore be achieved independently of the type of probe.

The method and the device are designed for the detection of magnetic leakage fields caused by defects, that is to say as a leakage flux test method and leakage flux test device, respectively. Corresponding leakage flux test probes can accordingly be designed as (passive) leakage flux probes which, in contrast to actively energized Eddy current probes, are not excited and accordingly do not themselves generate a magnetic field. A magnetic-field-sensitive leakage flux probe detects substantially only the inhomogeneities of the magnetic flux. The evaluation of the probe signals is accordingly designed for the evaluation of leakage flux signals, such that, e.g., impedance changes and/or changes in the magnetic resistance are not evaluated or do not have to be evaluated. The generation of the magnetization field is ensured by a separate magnetization apparatus decoupled from the test probe.

For the testing, a relative movement is preferably produced between the test sample and the magnetic constant field acting on the test sample, wherein the relative movement preferably has a relative speed component directed substantially in the direction of the magnetic field lines of the constant field within the test sample. If, by way of example, the magnetic constant field is coupled into the test sample such that its field lines within the test sample predominantly extend approximately in the circumferential direction and/or substantially perpendicularly to a longitudinal axis of the test sample, then the relative movement can be achieved by a relative rotation between the test sample and a constant field magnetization unit. What can be achieved by the relative movement, in particular by a relative rotation of magnetizing constant field and test sample, is that the strength of the magnetic constant field changes, e.g., periodically from the "point of view" of the test volume (but without changing its polarity). The temporally changing constant field can generate Eddy currents in the electrically conductive test sample material, which Eddy currents counteract a penetration of the constant field into the depths of the test sample and ensure that the magnetic constant field (or the magnetic induction generated thereby in the test sample material) is concentrated in the near-surface region of the test sample, where the magnetic alternating field is also effective, which fundamentally does not have an heavily large penetration depth into the material. The concentration of the induced magnetic flux attributed to the constant field in the vicinity of the test sample surface can greatly reduce the permeability of the test sample material there in such a way that substantially only the permeance of the test sample material, but not the permeability thereof, inhibits a penetration of the alternating field into the interior of the test sample. As a result, the penetration depth of the alternating field or of the induced magnetic flux attributed thereto can be increased by comparison with testing without simultaneous constant field magnetization. As a result of such a superposition of magnetic constant field and magnetic alternating field near the surface of the test sample in the detection region of the test probe, it is possible to improve the detection sensitivity for near-surface defects, in particular for near-surface concealed defects, compared to conventional methods.

The minimum value of the relative speed for obtaining an advantageous concentration of the magnetic induction (or of the magnetic flux density) in direct proximity to the surface of the test sample material is dependent, inter alia, on the permeability of the test sample material, on the geometry of the test sample and also on the geometry of the test arrangement (e.g., pole surfaces and pole spacing of poles of the constant field magnetization unit). In general, the component of the relative speed that is measured, e.g., in the direction of the constant field lines should be at least 0.3 m/s, wherein particularly favorable values may be, for example, in the range of 1 m/s to 5 m/s, e.g. around 3 m/s.

A relative rotation of test sample and magnetic constant field can be achieved, for example, by the constant field magnetization means being fitted to a rotary head such that they are moved around a test sample, wherein the test sample itself does not have to rotate about its axis. It is also possible for the test sample to rotate about its axis and for the constant field magnetization means to be fitted in a static fashion. A combination of both movements is also possible. With simultaneous longitudinal movement of the test sample through a rotary head, a helical scanning of the test sample surface is possible, which can be utilized for uninterrupted testing given suitable adaptation of the passage speed of the test sample and rotational speed of a rotary head.

The frequency of the magnetic alternating field can be optimized in particular with regard to the desired sensitivity for near-surface defects and the desired test throughput or the desirable scanning speed. Preferably, a magnetic alternating field is generated with an alternating field frequency of at least 1 kHz, wherein the alternating field frequency is preferably between 3 kHz and 12 kHz, for example, in the range of approximately 6 kHz to 8 kHz. Particularly in the range of between 3 kHz and 12 kHz, it is possible to obtain high surface sensitivities in conjunction with sufficiently high scanning speeds and correspondingly high test throughputs with uninterrupted testing.

It has been found that, for numerous test tasks it may be expedient if the magnetic field strength $H_{DC}$ of the constant field in the test volume has at least half the magnitude of, in particular at least the same magnitude as, the magnetic field strength $H_{AC}$ of the alternating field. In general, 20 times the alternating field strength $H_{AC}$ should not be exceeded. In some methods it may be expedient if a field strength ratio $H_{DC}/H_{AC}$ between the magnetic field strength of the constant field and the magnetic field strength of the alternating field of between 1 and 20 is used, in particular between 1 and 5. Crucial influencing factors for setting a suitable field strength ratio are, inter alia, the saturation induction of the test sample material and the fault depth. By setting an expedient field strength ratio $H_{DC}/H_{AC}$, it is possible to increase the detection depth of the combination method without significantly impairing the resolution for external faults.

If identical or electrically similar coil arrangements are used for generating the alternating field and the constant field, then the field strength ratio $H_{DC}/H_{AC}$ can be set or defined by a corresponding excitation current ratio $I_{DC}/I_{AC}$ between the current intensity $I_{DC}$ of the constant current and the current intensity $I_{AC}$ of the alternating current, such that the condition $0.5 \leq I_{DC}/I_{AC} \leq 20$, in particular $1 \leq I_{DC}/I_{AC} \leq 5$, can then also hold true. The excitation currents for constant field and alternating field generally lie in the range of one or a plurality of amperes to ensure a sufficient magnetization of the test volume.

In some examples, the magnetic field strength $H_{DC}$ of the constant field is between approximately 10% and 95% of the saturation field strength of the test sample material in the test volume, preferably between approximately 70% and approximately 85% of the saturation field strength. It is thereby possible in many cases to achieve better results than when there is full saturation of the material in the test volume.

Furthermore, it has been found to be expedient if a field strength sum $\Sigma H = H_{AC} + H_{DC}$ of the magnetic field strength $H_{DC}$ of the constant field and the magnetic field strength $H_{AC}$ of the alternating field is in the range of between 10% and 100%, in particular in the range of between approximately 70% and approximately 85%, of the saturation field strength of the test sample material. It is assumed that, as a result of the combined application of magnetic constant field and magnetic alternating field in the test sample material, a saturation region arises which extends, proceeding from the surface, into the material more deeply than in the case of pure alternating field magnetization. The material quality and the constitution of the outer surface (e.g., rough from rolling and/or covered in scale or bare) play a significant part in the setting of suitable field strengths or field strength ratios.

Preferably, the constant field and the alternating field are coupled into the test volume in such a way that the induced magnetic flux generated by the constant field and the induced magnetic flux generated by the alternating field have substantially the same orientation, that is to say can be characterized by substantially identically oriented field lines. This superposition "in the same sense" of magnetic alternating field (temporally rapidly changing polarity) and magnetic constant field (constant polarity, if appropriate temporal change in the field strength active in the test volume, or the strength of the induced magnetic flux that is effective in the test volume and is attributed to the constant field) in the test volume has proved to be particularly effective with regard to improving the detection sensitivity.

If the induced magnetic flux induced by the constant field is oriented transversely, in particular substantially perpendicularly, to the induced magnetic flux induced by the alternating field, it is possible primarily to obtain an improvement in the signal/noise ratio. This is because, independently of the relative orientations of constant field and alternating field, by the constant field that is effective in addition to the alternating field, it is possible to achieve a homogenization of the test volume with regard to permeability inhomogeneities and the effect of local cold deformations. As a result, depending on the material composition and type of production method, it is possible to give rise to a reduction in the interfering background or an improvement in the signal/noise ratio and an associated increased detection sensitivity particularly for small defects.

The same orientation of magnetic constant field and magnetic alternating field can be achieved structurally for example by virtue of the fact that the same coil arrangement (AC/DC coil arrangement) of the magnetization apparatus is used for generating the constant field and for generating the alternating field. However, it is also possible for an alternating field coil arrangement (AC coil arrangement) to be used for generating the alternating field and for a constant field coil arrangement (DC coil arrangement) separate from the alternating field coil arrangement to be used for generating the constant field. They can be arranged for producing different orientations or an identical orientation of the corresponding induced magnetic fluxes.

A device—suitable for carrying out the method—for detecting near-surface defects in a test sample consisting at least partly of ferromagnetic material has a magnetization apparatus for magnetizing a test volume of the test sample, and at least one magnetic-field-sensitive test probe for the detection of magnetic leakage fields caused by the defects. The magnetization apparatus comprises a constant field magnetization unit for generating a magnetic constant field and an alternating field magnetization unit for generating a magnetic alternating field superposed on the constant field in the test volume, the alternating field magnetization unit being able to be activated simultaneously with the constant field magnetization unit.

An assigned evaluation apparatus, which processes the signals of the at least one magnetic-field-sensitive test probe, is designed by virtue of suitable hardware and/or software to evaluate the detected inhomogeneities of the magnetic flux and to process them to form fault signals. Other changes in properties in the region of the test probe, e.g., changes in the resistance and/or impedance changes, are not evaluated in the case of a pure leakage flux evaluation.

In some examples, the magnetization apparatus has at least one AC/DC coil arrangement which is electrically connected or connectable simultaneously to an alternating voltage source and to a constant voltage source. With the aid of the AC/DC coil arrangement it is possible to have the effect that, in the test volume, the field lines of the alternating field extend substantially parallel to the field lines of the constant field.

In some examples, the magnetization apparatus has at least one alternating field coil arrangement (AC coil arrangement) connected to an alternating voltage source and at least one constant field coil arrangement (DC coil arrangement) separate from the alternating coil arrangement and connected to a constant voltage source. This makes it possible, as necessary, to couple the fields superposed on one another into the test volume such that the field lines generated by the alternating field extend transversely, for example, substantially perpendicularly, to the field lines generated by the constant field. A parallel orientation of the field lines of constant field and alternating field is also possible with separate coil arrangements.

In some examples, the magnetization apparatus comprises at least one magnetization yoke having a yoke core, on which an AC coil arrangement and a constant coil arrangement are wound. These can be spatially separated coil arrangements which are connected to electrically decoupled voltage sources. However, it is also possible for at least one combined AC/DC coil arrangement to be wound onto the magnetization yoke. At all events the common yoke core ensures that the alternating field and the superposed constant field have substantially the same orientation in the test volume.

There are numerous variants for realizing a device for combined AC/DC leakage flux testing. By way of example, the constant field magnetization unit can have a constant voltage source connected directly to a corresponding DC coil arrangement. In some examples, the constant field magnetization unit has an alternating voltage source and a rectifier which is connected to the alternating voltage source and at the outputs of which the constant voltage required for operating the DC coil arrangement can be tapped off. In the case of this variant, it is possible for an inductive transformer operating in a contactless fashion (e.g., rotary transformer) to be arranged between the alternating voltage source and the rectifier. This makes it possible, in a simple manner, to fit the voltage source for operating the constant field magnetization on a stationary part of a test device and the DC coil arrangement on a movable part of the test arrangement, for example, on a rotary head.

In simple devices it is possible to employ a fixed setting of the ratio between the field strengths of the magnetic alternating field and of the magnetic constant field. In some examples, however, it is provided that the alternating voltage source and the constant voltage source can be set independently of one another. This enables a particularly precise adaptation of the field strengths of alternating field and constant field and also of the corresponding field strength ratio to the test sample geometry and the test sample material, as a result of which the detection sensitivity can be optimized individually for each test process.

For the detection of the leakage flux in the case of the combined AC/DC magnetization, it is possible to use all known types of leakage flux test probes, in particular inductive test probes, Hall probes or GMR (giant magnetoresistance) sensors or combinations thereof, for example, including probe systems of the constructions mentioned in the introduction.

These and further features emerge from the description and the drawings, wherein individual features can be realized by themselves or as a plurality in the form of subcombinations and in other fields and can constitute advantageous and inherently protectable forms. Examples are illustrated in the drawings and explained in greater detail below.

FIG. 1 schematically shows an axial view of essential structural parts of a device 100 for detecting near-surface defects in ferromagnetic test material by means of leakage flux measurement. The test device 100, which is also referred to hereinafter as "leakage flux test device" or, in a shortened manner, as "test device," can be used, inter alia, for the near-production, nondestructive testing of elongated semifinished products having a circular cross section such as, for example, bar steel or round billets, or else for testing pipes.

The test device 100 has a rotary head, which can be rotated about a rotary head axis 112 and on which, in the case of the example, two leakage flux test probes 110A, 110B arranged on movable probe holding means are arranged in diametrically opposite fashion such that they rotate upon rotation of the rotary head about its axis 112 on circular paths of circulation around the test sample 150 substantially parallel to the rotary head axis 112 through the rotary head. Depending on the device, the rotary head can rotate, for example, at rotational speeds of between approximately 100 min$^{-1}$ and 3000 min$^{-1}$. The test material is normally simultaneously transported through the test head at speeds of up to 3 m/s. During the rotary movement, the test probes 110A, 110B slide on the substantially cylindrical surface 151 of the test sample and in the process scan the surface in an uninterrupted fashion on helical paths.

The test device has a magnetization apparatus for the magnetization of near-surface test volumes of the test sample 150. The magnetization apparatus includes two substantially U-shaped magnetization yokes 120A, 120B, which are fitted to the rotary head in diametrically opposite fashion and the free ends of which serve as pole shoes and are oriented at a small radial distance from the test sample surface substantially radially with respect to the test sample surface and are arranged approximately symmetrically on both sides of the respectively assigned test probe 110A, 110B. Two separate coil arrangements are wound on each of the yokes 120A, 120B, namely a constant field coil arrangement 135A, 135B connected to a constant voltage source 130A, 130B and an alternating field coil arrangement 145A, 145B connected to an alternating voltage source 140A, 140B. The alternating voltage sources 140A, 140B can be mutually separate alternating voltage sources or one and the same alternating voltage source; likewise, the constant voltage sources 130A, 130B can be formed by separate voltage sources or a common constant voltage source.

The alternating voltage source is able to generate alternating voltages in the range of approximately 3 kHz to approximately 12 kHz at current intensities of up to a plurality of amperes, e.g., up to 20 amperes or more, wherein the desired frequency and the desired current intensity can be set in a continuously variable manner within these ranges.

If a current is sent through a magnetization coil arrangement during the operation of the test device, then a magnetomotive force equal to the product of the current and the number of turns of the coil arrangement arises in the coil arrangement. The magnetomotive force drives an induced magnetic flux through the yoke and via the air gap formed between the pole shoes and the test sample surface also into near-surface volume regions of the test sample. From the closed magnetic circuits in the region of the magnetization yokes, FIG. 1 schematically shows the magnetic field lines leading from the pole shoes to the test sample surface, and also, by hatching, the magnetized near-surface volume regions of the test sample.

In the defect-free material, the magnetic flux generated in the test volume is spatially distributed substantially homogeneously, as is shown by way of example in the defect-free region near the lower leakage flux probe 110B. Hardly any leakage flux penetrates out of the test sample. By contrast, cracks or other defects in the material act as regions of increased magnetic reluctance, and so field components in the vicinity of a defect can be guided around the defect and can also be forced out of the material in the region near the surface. In this respect, FIG. 1 shows, for example, that the test specimen 150 has in the region of the upper leakage flux probe 110A an external fault 152 in the form of a crack 152 extending as far as the surface. In the region of the crack, magnetic field components are forced out of the material as leakage flux 155 and can be detected by means of the passive test probe 110A arranged near the surface, this test probe being moved relative to the surface 151, and can be converted into electrical signals. Since the measurement principle is known per se, further explanations are dispensed with here.

One special characteristic of the test device 100 is that the magnetization apparatus comprises a constant field magnetization unit for generating a magnetic constant field in the test volume and, in addition, a simultaneously activatable alternating field magnetization unit for generating a magnetic alternating field superposed on the constant field in the test volume. The constant field magnetization unit includes the constant voltage sources 130A, 130B and the constant field coil arrangements 135A, 135B, respectively, connected thereto, while the alternating field magnetization unit comprises the alternating voltage sources 140A, 140B with the alternating field coil arrangements 145A, 145B, respectively, connected thereto. Since a constant field coil arrangement and an alternating field coil arrangement are in each case wound on a common yoke core, the induced magnetic flux lines associated with the alternating field and the induced magnetic flux lines associated with the constant field have substantially the same orientation, that is to say that they extend substantially parallel to one another through the yoke and the test sample. The magnetic flux is coupled in substantially perpendicularly to the test sample surface or substantially perpendicularly to the longitudinal direction of the test sample. In this case, the induced magnetic flux lines extend, in particular, also parallel to one another through the test volume respectively lying in the detection region of the test probe. In the test sample, the induced magnetic flux extends largely in the circumferential direction, as a result of which this arrangement is particularly well suited to the detection of longitudinal faults, that is to say those defects which extend parallel or at relatively small angles with respect to the axial direction of the test sample.

During testing, the test device 100 is operated at least at times such that both the constant voltage sources and the alternating voltage sources are connected to the respective coil arrangements and activated, such that the test volume is simultaneously magnetized by means of a magnetic constant field and by means of a magnetic alternating field superposed on the constant field.

The magnetic alternating field, which can have, e.g., an alternating field frequency of approximately 6 kHz to 8 kHz, penetrates only as far as a relatively small penetration depth into the electrically conductive test sample material, on account of the skin effect. For the magnetic constant field, too, a concentration of the magnetic flux lines in the near-surface region of the test sample arises, as is indicated schematically by the hatched regions near the surface in FIG. 1. This forcing of the magnetic constant field (or of the associated induced magnetic flux) out of the test sample material arises as a result of the fact that the constant field magnetization means rotate with a high relative speed component in the circumferential direction around the test sample, such that the near-surface volume regions of the test sample, with regard to the magnetic constant field, too, are exposed to constantly changing magnetic field strengths which, however, in contrast to the magnetic alternating field, do not change the polarity. In this case, the rate of change of the constant field magnetization is primarily determined by the rotational speed of the rotation. As a result of the constant field that is constantly changing in terms of its strength, Eddy currents are induced in the test sample, and counteract penetration of the constant field into larger depths of the test sample material. This gives rise to a constant field concentration (concentration of the induced magnetic flux of the constant field) in the vicinity of the surface in that region which lies in the detection region of the test probe and which is also influenced by the higher-frequency alternating field and is therefore superposed with the alternating field in this region near the surface.

In many cases it has proved to be expedient if the test volume is not magnetized completely up to its material-specific saturation limit, but rather only to an extent such that the induced magnetic flux density within the test volume remains below the saturation limit. This gives rise, in the regions of defects 152, to relatively large differences in relative permeability $\mu_r$ between the region of the defect 152 and the surrounding material, thus resulting in a relatively great field displacement and hence a good detectability of the defect or defects. Good results can often be obtained if the magnetic field strength $H_{DC}$ of the constant field is set such that it is between approximately 70% and approximately 90% of the saturation field strength of the test sample material. With this apportioning of the constant field, the leakage field mechanism for the alternating field is still maintained to the greatest possible extent. The optimum ratio between the field strength of the constant field and the field strength of the alternating field can vary from test part to test part or from material to material and is generally ascertained in suitable test passes. To enable a variable setting on the test device, the constant voltage source(s) and the alternating voltage source(s) can be set in a continuously variable manner independently of one another.

FIG. 2 shows a schematic view of a static leakage flux test device 200 for testing rotating test samples, wherein the test sample 250 is a pipe which consists of ferromagnetic metal and which rotates about its pipe axis. Test samples composed of solid material are likewise possible. The magnetization apparatus for the magnetization of the test sample comprises a substantially U-shaped magnetization yoke 220, which is fitted in a stationary fashion and whose ends facing the test sample are shaped concave-cylindrically in accordance with the cylindrical outer surface of the test sample, such that a narrow air gap having a substantially uniform thickness is situated between the pole shoes formed by the ends and the test sample surface. For the electromagnetic generation of the magnetization field, a single combined AC/DC coil arrangement 235 is provided, which comprises two series-connected turns assemblies 225A, 225B, which are in each case wound onto the magnetization yoke 220 in the vicinity of the pole shoes. The coil arrangement 235 is connected to a combined constant voltage and alternating voltage source 230, which is designed to excite the coil arrangement with a constant current $I_{DC}$ and an alternating current $I_{AC}$ superposed on the constant current.

A test probe 210 is fitted between the pole shoes of the magnetization yoke, which test probe is mounted such that it is movable in the radial direction of the test sample and can be pressed onto the test sample surface by means of spring force and can be, in particular, a Hall probe, an inductive probe or a GMR probe. The induced magnetic flux lines illustrated schematically extend in the near-surface region of the test sample substantially parallel to the surface such that cracks arranged radially or obliquely with respect to the radial direction in the test volume function as magnetic reluctances which cause a leakage flux that can be detected by the test probe 210. In this example, too, the induced magnetic flux lines generated by the constant field and the induced magnetic flux lines generated by the simultaneously active alternating field extend in the same direction since they are generated by one and the same coil arrangement and the same magnetization yoke.

In FIG. 2, the field lines extending in the test sample 250 indicate that, in this variant, too, the magnetic flux lines of the constant field and of the alternating field which extend in the same sense (parallel to one another) are concentrated in the near-surface region of the test sample, that is to say in the region facing the magnetization means, and do not penetrate very far to the interior. As in the example described above, this can be understood for the alternating field component. The fact that the constant field component also remains concentrated in the region near the surface is substantially due to the relative movement—extending (also) in the circumferential direction of the test sample—between the test sample and the magnetic constant field acting on it. The relative speed component extending in the circumferential direction of the test sample and therefore also in the direction of the between the poles of the magnetization yoke 220 should be more than 0.3 m/s, in particular more than 1 m/s to obtain an effective constant field concentration in the region of the surface.

FIG. 3 shows essential parts of a leakage flux test device 300 for the continuous testing of round material. The test device has a rotary head, through which the test sample 350 runs and to which are fitted, at diametrically opposite positions, magnetization yokes 320A, 320B with ends facing one another, which respectively carry alternating coil arrangements 345A, 345B, which are connected in series and are connected to a common alternating voltage source 340. The rotary head additionally carries a plurality of leakage flux test probes 310 arranged in a manner angularly offset by 90° with respect to the poles formed on the magnetization yoke. On a stationary component of the test device 300, an annular coil arrangement 335 is arranged in a manner axially offset with respect to the rotary head coaxially with respect to the latter, the arrangement being connected to a constant voltage source 330. Consequently, in the case of this rotating test system with static DC magnetization and rotating AC magnetization, there is a spatial separation of the constant field magnetization unit and the alternating field magnetization unit. The structural complexity and associated costs can thereby be kept particularly low. Since the central coil axis of the DC coil arrangement 335 is oriented coaxially with respect to the rotary head and the test sample 350 is led through the test device substantially coaxially with respect to this common axis, the constant field coil arrangement 335 generates, when the constant voltage source is activated, a magnetic constant field whose flux lines 336 extend at least in the vicinity of the constant field coil arrangement 335 substantially parallel to the longitudinal axis of the test sample. By contrast, the induced magnetic flux lines 346 of the magnetic alternating field that are generated by the alternating field coil arrangements 320A, 320B extend substantially in a plane perpendicular to the longitudinal axis of the test sample and hence also substantially perpendicular to the induced magnetic flux lines of the magnetic constant field.

Figure 4:
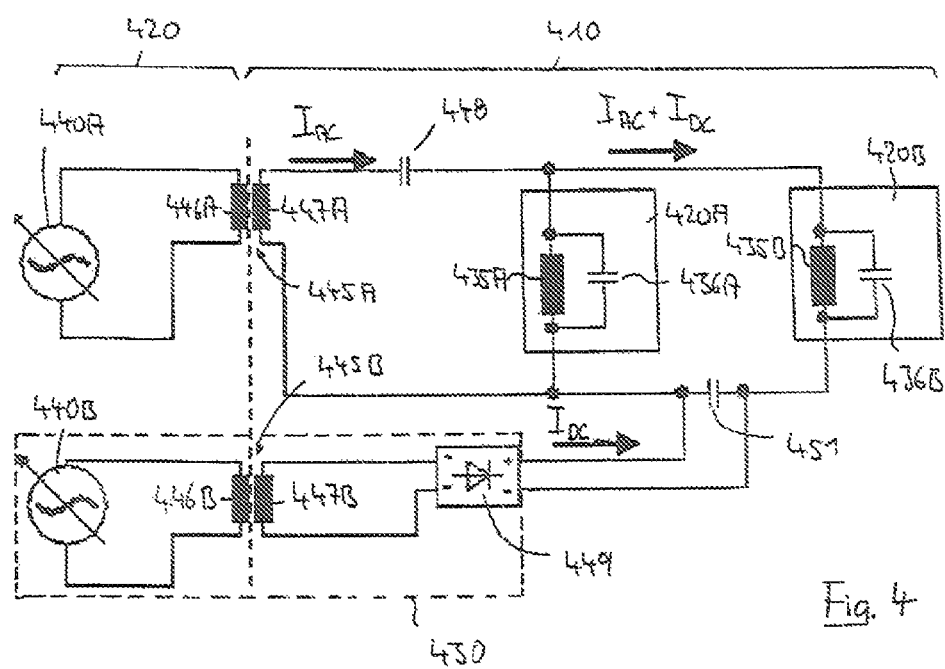
FIG. 4 schematically shows a circuit arrangement for a combined AC/DC magnetization with two identical magnetization yokes each carrying a combined AC/DC coil arrangement.

FIG. 4 shows an example of a circuit arrangement for a magnetization apparatus of a leakage flux test device with combined constant field/alternating field magnetization. The magnetization apparatus has two identically constructed magnetization yokes 420A, 420B, wherein an AC/DC coil arrangement 435A and 435B, respectively, for generating the magnetization field is wound onto each of the yokes. Capacitances (symbolized by capacitors 436A, 436B) are respectively connected in parallel with the inductances of the coil arrangements 435A, 435B such that the coil arrangements 435A, 435B are respectively linked into a tuned circuit. In a manner similar to that in the case of the example in FIG. 1, the magnetization yokes are fitted to a rotary head 410, which can be rotated about a rotary head axis relative to a static part 420 of the test device.

For the electrical power supply of the magnetization apparatus, two alternating voltage sources 440A, 440B which can be set in a continuously variable manner independently of one another are accommodated in the stationary part 420 of the test device. The electrical connection between the alternating voltage sources in the stationary part 420 and the electrical components of the rotary head 410 is achieved by inductive rotary transformers 445A, 445B. In this case, the first alternating voltage source 440A is connected to the primary winding 446A of the first rotary transformer 445A, and the second alternating voltage source 440B is connected to the primary-side winding 446B of the second rotary transformer 445B. The secondary-side winding 447A of the first rotary transformer 445A is connected, at one end, via a capacitor 448 in each case to one end of the coil arrangement 435A, 435B connected in parallel with respect to the alternating voltage. The other terminal of the secondary winding 447A is electrically connected in each case to the opposite terminal of the coil arrangement 435A and 435B, respectively.

The second alternating voltage source 440B is connected to the rotating parts of the electrical arrangement via a second rotary transformer 445B having a primary-side winding 446B and a secondary-side winding 447B. The ends of the secondary winding 447B are in each case connected to the inputs of a rectifier 449, the outputs of which thus form the outputs of a constant voltage source 430 comprising the second alternating voltage source 440B, the second rotary transformer 445B and the rectifier 449. From the "+" output of the constant voltage source 430, a constant current circuit leads through the coil arrangement 435A of the first yoke 420A, the coil arrangement 435B—connected in series therewith with respect to constant current—of the second magnetization yoke 420B to the "−" output of the constant voltage source 430. A capacitor 451 connected between the outputs of the constant voltage source ensures that the AC/DC coil arrangements 435A, 435B are connected in series with one another with respect to the constant current and in parallel with one another with respect to the alternating current.

Upon simultaneous activation of the first and second alternating voltage sources 440A, 440B, a constant current $I_{DC}$ on which an alternating current $I_{AC}$ is superposed flows through the two coil arrangements 435A, 435B. In this case, the constant current component $I_{DC}$ is provided by the constant current source 430, while the alternating current component $I_{AC}$ is provided directly by the first alternating voltage source 440A by means of the first rotary transformer 445A. By setting the power ratio between the alternating voltage sources 440A, 440B, the ratio of the current intensities between alternating current and constant current and hence also the ratio of the magnetization field strengths of electric constant field and electric alternating field can be set in a continuously variable manner. The tuned circuits with the coil arrangements 435A and 435B, respectively, are in each case tuned as resonant tuned circuits, such that only leakage current has to be fed.

The alternating voltage sources 440A, 440B can also be activated alternately such that the magnetization apparatus can also be operated as a pure constant field magnetization apparatus or as a pure alternating field magnetization apparatus.

Essential advantages of the combined constant field/alternating field magnetization are explained below on the basis of some examples. As mentioned in the introduction, a test device with combined AC and DC magnetization has a significantly larger penetration depth on the test material by comparison with a pure alternating field magnetization. What can thereby be achieved is that very deep material faults such as, e.g., stress cracks which are not open at the surface or faults that have been rolled in by the manufacturing process are indicated with a signal amplitude which is comparable to that of a fault which is open to the surface. In addition, it has been observed that a homogenization of the test parts with regard to permeability inhomogeneities and the effect of local cold deformations can occur as a result of the constant field that is effective in addition to the alternating field. As a result, depending on the material composition and type of production method, a reduction in the interfering background can be obtained. These advantages will become clear from the following test results.

Figure 5:
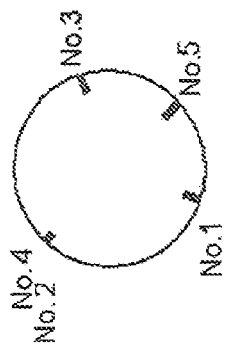
FIG. 5 shows the geometry of an experimental test part having four different faults open to the surface and a concealed fault.
Figure 5:
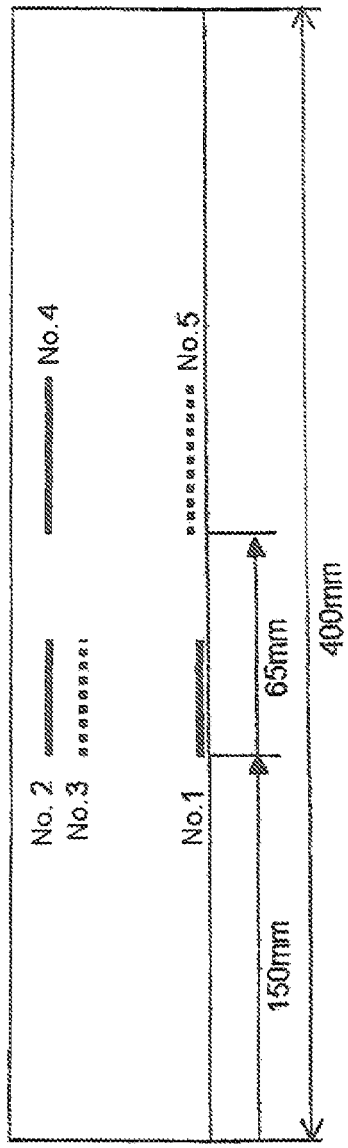
Figure 5:
Figure 5:
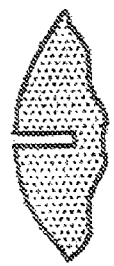

To check the effects of a simultaneous AC/DC magnetization on the quality of the fault signals, an experimental test part explained with reference to FIG. 5 was produced. The test part composed of cold-drawn steel material had a circular-cylindrical cross section (FIG. 5B) having a diameter of 40 mm and a length of 400 mm. On the circumference of the test part, a total of five longitudinal faults (fault orientation parallel to the longitudinal axis of the test part) were introduced by sawing cuts in the manner evident from FIG. 5A. The characteristics of all the faults can be gathered from Table A below:

TABLE A

| | Fault size | | | | |
|---|---|---|---|---|---|
| No. | Depth [mm] | Width [mm] | Length [mm] | Direction Longitudinal | Production Sawn |
| 1 | 0.1 | 0.2 | 50 | X | X |
| 2 | 0.3 | 0.2 | 50 | X | X |
| 3 | 1.0 | 0.2 | 50 | X | X |
| 4 | 8.1 | 0.2 | 60 | X | X |
| 5 | 8.1 | 0.2 | 60 | X | X rolled in |

The faults had in each case the same width (0.2 mm) and in part different depths and lengths, wherein the faults Nos 1 to 4 in accordance with FIG. 5C as open faults were open to the surface of the test sample, while fault No. 5 was embodied as a rolled-over sawing cut, that is to say as a concealed fault whose air-filled disturbance zones does not quite extend as far as the surface because the production of the notch was followed by a rolling step which led to a superficial closure of the sawing cut. The concealed fault No. 5 otherwise has the same dimensions as the open fault No. 4. The test part was led through a static, combined AC/DC leakage flux test device at a speed of approximately 0.2 m/sec and in the process was rotated about its longitudinal axis, e.g., with rotational speeds of between 300 rpm and 2400 rpm. The alternating voltage source was set to a frequency of 7.5 kHz, which is in the range of the typical frequencies for AC leakage flux measurements (approximately 3 kHz to approximately 12 kHz). A constant current of $I_{DC} \approx 20$ A and an excitation current ratio $I_{DC}/I_{AC}$ between the current intensity $I_{DC}$ of the constant current and the current intensity $I_{AC}$ of the alternating current of approximately 4:1 were set by means of the constant voltage and alternating voltage sources. A combined constant field/alternating field coil arrangement was used, such that a corresponding field strength ratio $H_{DC}/H_{AC} \approx 4:1$ was produced in the test material.

Figure 6A:
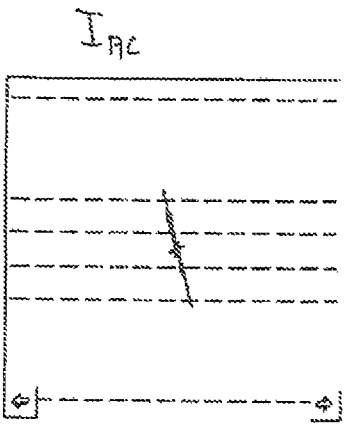
FIGS. 6 and 7 show illustrations of the fault amplitudes produced by the faults in the impedance plane.
Figure 6B:
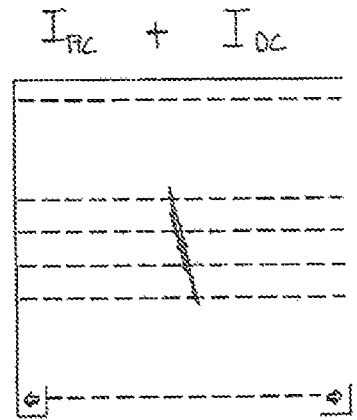
Figure 7A:
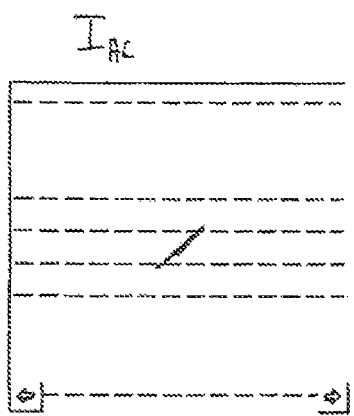
Figure 7B:
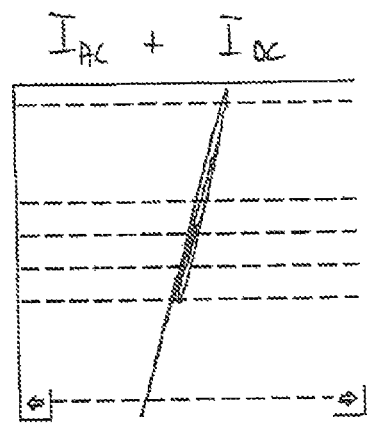

FIGS. 6 and 7 each show illustrations of the fault amplitudes produced by the faults in the impedance plane. In this case, the length of the elongated signal represents the fault amplitude, while the orientation of the signal in the impedance plane represents the relative phase of the fault amplitude with respect to a reference position. FIG. 6 shows the results for fault No. 2 (open fault, 0.3 mm deep, 0.2 mm wide), while FIG. 7 shows the results for fault No. 5 (concealed fault, 8.1 mm deep, 0.2 mm wide, rolled in, cf. FIG. 5D). The figures respectively on the left, FIG. 6A and FIG. 7A, in each case show the signal for pure alternating field magnetization with $I_{AC} \approx 5$ A and $I_{DC}=0$ A. The figures respectively on the right, FIGS. 6B and 7B, show the signals for combined constant field/alternating field magnetization, wherein a magnetic constant field generated by means of constant current of $I_{DC} \approx 20$ A was superposed on the unchanged alternating field ($I_{AC} \approx 5$ A).

The comparison of the signals in FIGS. 6A and 6B shows that the relatively small open fault in the case of the combined constant field/alternating field magnetization (FIG. 6B) has substantially the same fault amplitude and phase angle as in the case of the pure alternating field excitation (FIG. 6A). Therefore, the additional constant field magnetization does not lead to an impairment of the sensitivity of the method with alternating field magnetization. By contrast, distinct differences arise in the case of the concealed fault No. 5 closed to the surface. While the test with pure alternating field excitation (FIG. 7A) shows a relatively small fault signal, the reliable evaluation of which requires careful separation of the actual fault signal from the interfering background, the combined constant field/alternating field magnetization (FIG. 7B) brings a clear fault signal with a multiply greater fault amplitude. It is thus evident that the combined constant field/alternating field magnetization affords considerable advantages over the pure alternating field magnetization precisely in the case of open faults which do not extend as far as the surface. Moreover, the comparison of the fault amplitudes of the relatively deep fault No. 5 in FIG. 7B and of the—in relation thereto—shallower fault No. 2 in FIG. 6B shows that the fault amplitude is greatly dependent on the fault depth.

Figure 8A:
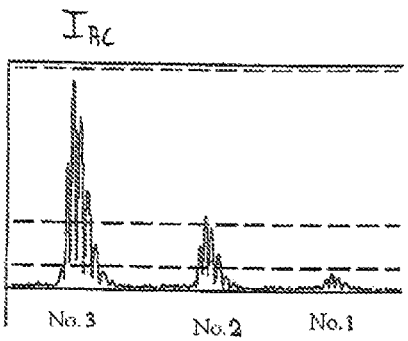
FIGS. 8 and 9 show circumference-related illustrations of the fault amplitudes.
Figure 8B:
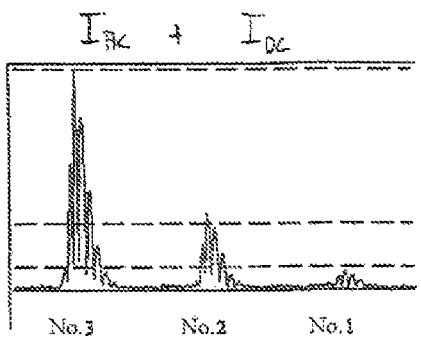
Figure 9A:
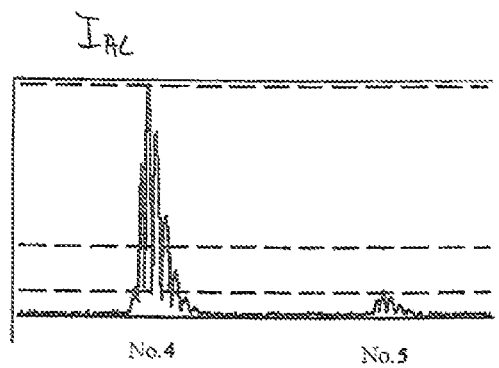
Figure 9B:
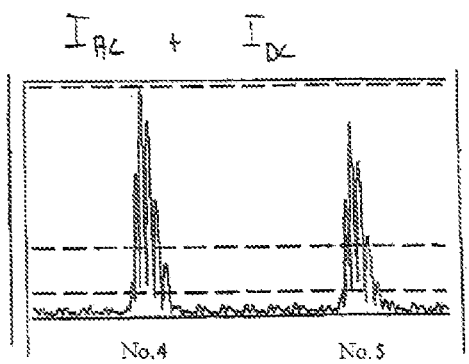

FIGS. 8 and 9 show circumference-related illustrations of the fault amplitudes, wherein the left-hand FIGS. 8A, 9A in each case show the results of the pure alternating field magnetization and the right-hand FIGS. 8B, 9B in each case show the results for the combined DC field/AC field magnetization. The illustrations in FIG. 9 result from detection with reduced sensitivity in comparison with the illustrations in FIG. 8, but are directly comparable among one another. It is evident from the illustrations in FIG. 8 that the combined AC/DC magnetization, in comparison with the pure alternating field magnetization, brings practically identical fault amplitudes in the case of faults which are open to the surface, and so there is no need to fear any losses in respect of resolution capability. The comparison of the faults No. 4 (open fault) and No. 5 (rolled-in, concealed fault) in FIG. 9 shows, by contrast, that the combined constant field/alternating field magnetization (FIG. 9B), for the rolled-in fault No. 5, produces a considerably greater fault amplitude than the pure alternating field magnetization (FIG. 9A). The fault signal stands out distinctly from the interfering background, which makes it clear that the combined constant field/alternating field magnetization affords considerable advantages over the pure alternating field magnetization particularly in the detection of concealed faults, without giving rise to disadvantages in the case of the faults which are open to the surface.

My methods and devices can be used for a wide variety of types of test sample, for example, for tubular test samples and equally for test samples composed of solid material. A test sample can have a circular cross section, as a result of which a relative rotation of test sample and test probe becomes possible in a particularly simple manner, which can be brought about by rotation of the test sample, by rotation of that part of the test device contained the probe(s) and/or by a combination of these rotations. Test samples having a non-circular cross section, for example, triangular billets or square billets or billets having other polygonal cross sections, and test samples having an elliptical cross section, can also be tested, in which case, if appropriate, the relative movement between test sample and test probe can then be brought about substantially by the movement of the test sample relative to a static test device.

The invention claimed is:

1. A method of detecting near-surface defects in a test sample consisting at least partly of ferromagnetic material, wherein a test volume of the test sample is magnetized and scanned to detect magnetic leakage fields caused by defects, and the test volume is magnetized by a magnetic constant field and simultaneously by a magnetic alternating field superposed on the constant field,
wherein
the constant field and the alternating field are coupled into the test volume such that the induced magnetic flux generated by the constant field and the induced magnetic flux generated by the alternating field have substantially the same orientation,
a relative movement is produced between the test sample and the magnetic constant field acting on the test sample, and the relative movement has a relative speed component directed substantially in the direction of the magnetic field lines of the constant field within the test sample,
a component of the relative speed that is measured in the direction of the field lines of the constant field is at least 0.3 m/s, and
a magnetic alternating field is generated with an alternating field frequency of at least 1 kHz.

2. The method as claimed in claim 1, wherein the magnetic constant field is coupled into the test sample such that field lines of the magnetic constant field within the test sample extend in sections approximately in a circumferential direction and/or substantially perpendicularly to a longitudinal axis of the test sample, wherein the relative movement is achieved by a relative rotation between the test sample and a constant field magnetization unit.

3. The method as claimed in claim 1, wherein the alternating field frequency is preferably between 3 kHz and 12 kHz.

4. The method as claimed in claim 1, wherein the magnetic field strength $H_{DC}$ of the constant field in the test volume has at least half the magnitude of the magnetic field strength $H_{AC}$ of the alternating field and/or is not more than 20 times the magnetic field strength of the alternating field.

5. The method as claimed in claim 1, wherein a field strength ratio $H_{DC}/H_{AC}$ between the magnetic field strength $H_{DC}$ of the constant field and the magnetic field strength $H_{AC}$ of the alternating field is between 1 and 5.

6. The method as claimed in claim 1, wherein the magnetic field strength $H_{DC}$ of the constant field is between approximately 10% and approximately 95% of the saturation field strength of the test sample material in the test volume.

7. The method as claimed in claim 1, wherein a field strength sum $\Sigma H = H_{AC} + H_{DC}$ of the magnetic field strength $H_{DC}$ of the constant field and the magnetic field strength $H_{AC}$ of the alternating field is between approximately 10% and approximately 100% of the saturation field strength of the test sample material in the test volume.

8. The method as claimed in claim 1, wherein the same coil arrangement is used to generate the constant field and to generate the alternating field.

9. The method as claimed in claim 1, wherein an alternating field coil arrangement is used to generate the alternating field and a constant field coil arrangement separate from the alternating field coil arrangement is used to generate the constant field.

10. The method as claimed in claim 1, wherein the magnetic leakage fields are detected with the aid of at least one magnetic-field-sensitive leakage flux probe and an evaluation of probe signals of the leakage flux probe is designed to evaluate leakage flux signals, wherein, an amplitude of the probe signal is evaluated to characterize defects.

11. A device that detects near-surface defects in a test sample consisting at least partly of ferromagnetic material, comprising:
a magnetization apparatus for magnetizing a test volume of the test sample, and
at least one magnetic-field-sensitive test probe that detects magnetic leakage fields caused by defects, wherein the magnetization apparatus comprises a constant field magnetization unit that generates a magnetic constant field and an alternating field magnetization unit that generates a magnetic alternating field superposed on the constant field in the test volume,
wherein
the constant field and the alternating field are coupled into the test volume such that the induced magnetic flux generated by the constant field and the induced magnetic flux generated by the alternating field have substantially the same orientation, a relative movement is produced between the test sample and the magnetic constant field acting on the test sample, and the relative movement has a relative speed component directed substantially in the direction of the magnetic field lines of the constant field within the test sample, a component of the relative speed that is measured in the direction of the field lines of the constant field is at least 0.3 m/s, and a magnetic alternating field is generated with an alternating field frequency of at least 1 kHz.

12. The device as claimed in claim 11, wherein the magnetization apparatus has at least one alternating field/constant field coil arrangement which is electrically connected or connectable simultaneously to an alternating voltage source and to a constant voltage source.

13. The device as claimed in claim 11, wherein the magnetization apparatus has at least one alternating voltage coil arrangement connected to an alternating voltage source and at least one constant voltage coil arrangement separate from the alternating voltage coil arrangement and connected to a constant voltage source.

14. The device as claimed in claim 11, wherein the magnetization apparatus has at least one magnetization yoke having a yoke core, on which an alternating voltage coil arrangement and a constant voltage coil arrangement are wound.

15. The device as claimed in claim 14, wherein the alternating voltage coil arrangement is wound on the yoke core spatially separately from the constant voltage coil arrangement.

16. The device as claimed in claim 11, wherein the alternating voltage coil arrangement and the constant voltage coil arrangement are formed by the same coil arrangement.

17. The device as claimed in claim 11, wherein the alternating voltage unit and the constant voltage unit can be set independently of one another.

18. The device as claimed in claim 11, wherein an alternating voltage source of the alternating field magnetization unit generates alternating voltages of 3 kHz to 12 kHz and/or current intensities of up to a plurality of up to 20 amperes or more.

19. The device as claimed in claim 11, further comprising an apparatus that produces a relative movement between the test sample and the magnetic constant field acting on the test sample, wherein the relative movement has a relative speed component directed substantially in the direction of the magnetic field lines of the constant field within the test sample.

20. The device as claimed in claim 11, wherein the constant field magnetization unit is on a rotary head such that it can be moved around the test sample.

21. The device as claimed in claim 11, wherein the constant field magnetization unit is arranged such that the magnetic constant field is coupled into the test sample such that field lines of the magnetic constant field within the test sample extend in sections approximately in a circumferential direction and/or substantially perpendicularly to a longitudinal axis of the test sample.

22. The device as claimed in claim 11, further comprising an evaluation apparatus that processes probe signals of the at least one magnetic-field-sensitive test probe, wherein the evaluation apparatus evaluates magnetic flux inhomogeneities detected by the test probe and processes them to form fault signals, wherein, a fault amplitude of the fault signal is evaluated to characterize defects.

23. A device that detects near-surface defects in a test sample consisting at least partly of ferromagnetic material, comprising:

a magnetization apparatus for magnetizing a test volume of the test sample, and at least one magnetic-field-sensitive test probe that detects magnetic leakage fields caused by defects, wherein the magnetization apparatus comprises a constant field magnetization unit that generates a magnetic constant field and an alternating field magnetization unit that generates a magnetic alternating field superposed on the constant field in the test volume, wherein the constant field magnetization unit comprises an alternating voltage source and a rectifier connected to the alternating voltage source.

24. The device as claimed in claim 23, wherein an inductive transformer operating in a contactless fashion is arranged between the alternating voltage source and the rectifier.

25. The device as claimed in claim 14, wherein the magnetization yoke is a substantially U-shaped magnetization yoke, free ends of which serve as pole shoes and are oriented substantially radially with respect to the test sample surface, and wherein the pole shoes are arranged approximately symmetrically on both sides of an assigned test probe.

26. The device as claimed in claim 19, wherein the relative movement comprises a relative rotation between the test sample and the constant field magnetization unit.

* * * * *